(12) United States Patent
Sato (10) Patent No.: US 6,814,703 B2
(45) Date of Patent: Nov. 9, 2004

(54) APPARATUS AND METHOD FOR ULTRASONIC DIAGNOSTIC IMAGING USING A CONTRAST MEDIUM

(75) Inventor: Takeshi Sato, Tochigi-ken (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 10/259,760

(22) Filed: Sep. 30, 2002

(65) Prior Publication Data

US 2003/0073903 A1 Apr. 17, 2003

(30) Foreign Application Priority Data

Sep. 28, 2001 (JP) ........................................ 2001-304013

(51) Int. Cl.[7] ................................................. A61B 8/06
(52) U.S. Cl. ...................................................... 600/458
(58) Field of Search ........................ 600/437, 440–441, 600/443, 447, 453–456, 458

(56) References Cited

U.S. PATENT DOCUMENTS

| | | | | |
|---|---|---|---|---|
| 5,445,156 A | * | 8/1995 | Daft et al. ................... | 600/454 |
| 5,623,930 A | * | 4/1997 | Wright et al. ................ | 600/447 |
| 5,718,229 A | * | 2/1998 | Pesque et al. .............. | 600/441 |
| 5,931,784 A | * | 8/1999 | Kajiwara et al. ............ | 600/441 |
| 6,095,980 A | | 8/2000 | Burns et al. | |
| 6,171,246 B1 | * | 1/2001 | Averkiou et al. ............ | 600/458 |
| 6,210,334 B1 | * | 4/2001 | Phillips ....................... | 600/453 |
| 6,497,665 B1 | * | 12/2002 | Hunt et al. ................. | 600/458 |

OTHER PUBLICATIONS

Pulse inversion Doppler: A new Method for Detecting Nonlinear Echoes from Microbubble Contrast Agents, IEEE Transactions on Ultrasonics, Ferroelectrics, and Frequency Control, vol. 46, No. 2, Mar. 1999, pp. 372–382.

* cited by examiner

Primary Examiner—Francis J. Jaworski
(74) Attorney, Agent, or Firm—Oblon, Spivak, McClelland, Maier & Neustadt, P.C.

(57) ABSTRACT

An ultrasonic diagnostic apparatus and method are disclosed that use a contrast echo method, which can obtain an ultrasonic image indicating proper blood flow directions and distinguishably showing blood flow, enhancement in parenchyma and tissues with no enhancement. A method is performed with low mechanical index transmission to create B-mode, velocity and power signals and these signals are compared to determine a value for each pixel. Thus, tissues with no contrast-enhancement can be displayed with the B signal value in gray scale, parenchyma with contrast-enhancement with P and/or V values in dark green, slow blood flow (such as a vein) with P and/or V values in bright green and fast blood flow (such as an artery) with P and/or V values in red or blue according to the direction of the flow.

20 Claims, 9 Drawing Sheets

9 (a) Before contrast medium injection
(Only B-mode image is displayed)

9 (b) Blood flow is enhanced 9 (c) Parenchyma is enhanced 9 (d) Enhancement in blood flow is vanishing 9 (e) Spleen is still enhanced
No enhancement in blood flow (red/blue)
Enhancement only in parenchyma (green)

APPARATUS AND METHOD FOR ULTRASONIC DIAGNOSTIC IMAGING USING A CONTRAST MEDIUM

CROSS-REFERENCE TO RELATED APPLICATIONS

This application is based upon and claims the benefit of priority from the prior Japanese Patent Application No. 2001-304013, filed Sep. 28, 2001, the entire contents of which are incorporated herein by reference.

TECHNICAL FIELD OF THE INVENTION

The present invention relates to an ultrasonic diagnostic apparatus capable of diagnosis with contrast echo method using contrast medium.

BACKGROUND OF THE INVENTION

An ultrasonic apparatus can noninvasively obtain a tomographic image of soft tissues inside a living body from the surface of the body using reflection of an ultrasonic wave and has advantages such as compactness, low price, capability of real time imaging, increased safety due to a lack of X-ray dosing, capability of blood flow imaging, etc., when compared to other diagnostic devices, such as X-ray diagnostic apparatus, X-ray CT apparatus, MRI apparatus or nuclear medicine diagnostic apparatus, and the like. Because of such advantages, ultrasound is currently widely used in many medical fields such as cardiac medicine, abdominal medicines such as gastroenterology, urology, obstetrics, gynecology, as well as others.

There are a variety of imaging methods for the ultrasonic diagnostic apparatus. "Contrast Echo" method is one of the important techniques to obtain an ultrasonic image in which scattered echo signals are enhanced by using an ultrasonic contrast medium containing microbubbles injected into a blood vessel of an object.

Recently, new contrast media for intravenous injection have emerged and imaging methods suitable for these contrast media have also been developed. For example, such methods include a Filter method (an imaging method using one pulse per scan line: U.S. Pat. No. 5,678,553), a Doppler method (an imaging method using more than two in-phase pulses per scan line), a Phase Inversion method (an imaging method using two 180° out-of-phase pulses per scan line: U.S. Pat. No. 5,632,277), a Phase Inversion Doppler method (an imaging method using more than three pulses alternated by 180° from pulse to pulse per scan line: U.S. Pat. No. 6,095,980), the contents of which are herein incorporated by reference.

When performing a Contrast Echo method with any of the above methods, conventionally ultrasonic waves with medium or high acoustic pressure, such as MI (mechanical index) value of more than 0.5 have been used. This is typically done to obtain a prominent contrast enhancement effect by collapsing the microbubbles in the contrast medium. For example, when using one of widely used contrast medium, Levovist, manufactured by Schering, the image may not be properly enhanced unless ultrasonic waves with high acoustic pressure, such as those having an MI value of more than 0.8 are used.

Transmission of ultrasonic waves with high acoustic pressure and the subsequent collapse of microbubbles greatly affects ultrasonic imaging. When an ultrasonic wave with high acoustic pressure is propagated through tissue, a harmonic component is generated in an echo. However, the above-mentioned Filter method or Phase Inversion method can not separate a harmonic component from tissues (hereinafter "THI component") from a harmonic component from bubbles. Accordingly an image of bubbles obtained with the Filter method or the Phase Inversion method may not have enough contrast, and it may be difficult to distinguish between blood flow and a parenchymal contrast-enhancement in a contrast echo image.

Further, a collapse of bubbles creates a broadband echo signal when more than two ultrasonic beams are transmitted per scan line. This broadband echo signal, called a pseudo-Doppler signal, can be utilized to produce an image by suppressing tissue and THI components in the fundamental signal.

However, a color Doppler image based on the pseudo-Doppler signals would result in an image of thin blood vessels and contrast-enhancement in parenchyma with many aliasing points, which does not indicate proper blood flow velocities or directions unlike a normal Doppler signal. Therefore, in most cases when an ultrasonic image obtained with contrast echo method is displayed, power Doppler is used instead of color Doppler, which is generally suitable for showing blood flow velocity.

BRIEF SUMMARY OF THE INVENTION

It is accordingly an aspect of the present invention to provide an ultrasonic diagnostic apparatus, including an image processing unit capable of producing an ultrasonic image from the echo signal, where each pixel in an ultrasonic image has a brightness and a color, each of which is adjusted according to information on blood flow in a subject. The ultrasonic beam used to generate the ultrasonic image is transmitted with a mechanical index value configured to collapse microbubbles to an extent that an echo signal contains the information on blood flow in an object used to adjust the brightness and the color.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Referring now to the drawings, where like reference numeral designations identify the corresponding parts throughout the several views, several embodiments of the present invention are next described.

First Embodiment

Figure 1:
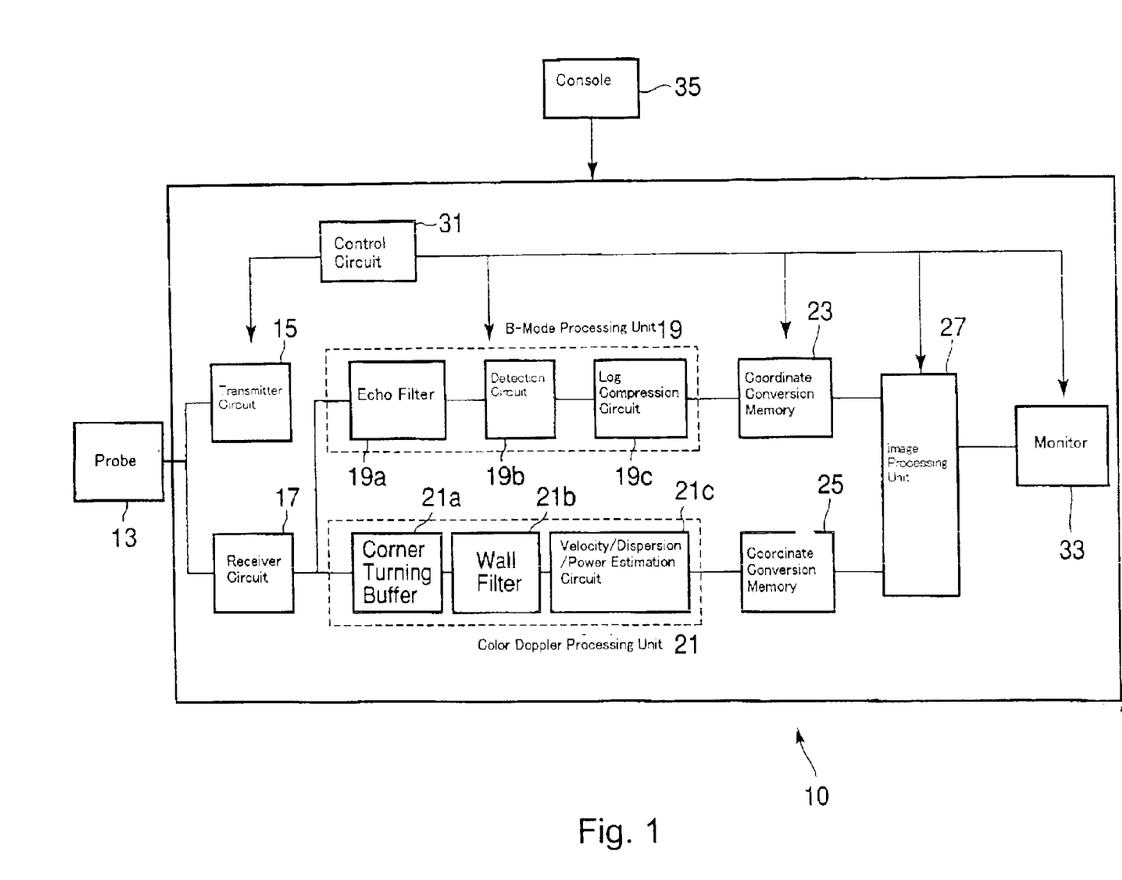
FIG. 1 shows a block diagram of an ultrasonic diagnostic apparatus of a first embodiment of the invention.

FIG. 1 shows a block diagram of an ultrasonic diagnostic apparatus 10 according to a first embodiment of the present invention. The ultrasonic diagnostic apparatus includes an ultrasonic probe 13, a transmitter circuit 15, a receiver circuit 17, a B-mode processing unit 19, a color Doppler processing unit 21, a coordinate conversion memory for B-mode processing 23, a coordinate conversion memory for color Doppler processing 25, an image processing circuit 27, a control circuit 31, a monitor 33, and a console 35. The ultrasonic probe 13 includes piezoelectric transducers. The piezoelectric transducers, provided on the top of the probe in an array, transmit ultrasonic waves according to exciting pulses applied from the transmitter circuit 15. The transmitter circuit 15, connected to the probe 13, includes a pulse generator, a transmission delay circuit and a pulser (not shown in FIG. 1). The pulse generator in the transmitter circuit 15 repeatedly generates rate pulses at a rate frequency fr (Hz) (cycle: 1/fr (sec.)) of 5 kHz. These rate pulses are distributed to each channel to be sent to the transmission delay circuit. The transmission delay circuit provides each of the rate pulses with a delay time useful for concentrating ultrasonic waves to form a beam and determining the transmission directivity. The transmission delay circuit is triggered by timing signals from a trigger signal generator (not shown). The pulser provides each channel in the probe 13 with a voltage pulse when it receives the rate pulse from the transmission delay circuit.

The receiver circuit 17 includes a preamplifier, an A/D converter, a reception delay circuit and an adder. The preamplifier amplifies an echo signal received in the receiver circuit 17 through the probe 13 at each channel. The amplified echo signal is provided with a delay time necessary for determining the reception directivity and added in the adder. This adding process produces an echo signal (RF signal) in which components reflected from directions according to the reception directivity of the echo signal are enhanced. The reception and transmission directivities determine the total directivity, or "scan line" of the ultrasonic transmission and reception.

The B-mode processing unit 19 includes an echo filter 19a, detection circuit 19b and a log compression circuit 19c. The echo filter 19a is a band pass filter for phase detection and sampling of echo signals in a desired frequency band. The detection circuit 19b detects an envelope of an echo signal output from the echo filter 19a and obtains a B-mode signal constituting a B-mode image, in which fundamental components are imaged, for each scan line according to the procedures described later. The log compression circuit 19c performs logarithmic compression on the B-mode detection data.

The color Doppler processing unit 21 includes a CTB (Comer Turning Buffer) 21a, a wall filter 21b and a velocity/dispersion/power estimation circuit 21c. The CTB 21a is a device for temporally storing a color Doppler data array. The data array in the CTB 21a is output to the wall filter 21b according to a predetermined order. The wall filter 21b, in this embodiment, functions as a low pass filter for separating a harmonic component from a fundamental component as described in detail later. The velocity/dispersion/power estimation circuit 21c is a circuit for calculating correlations of the signals according to a plurality of echo signals being different in phase and obtaining an average frequency. A velocity/dispersion/power estimation of blood flow in color Doppler is calculated by the velocity/dispersion/power estimation circuit 21c. velocity/dispersion/power estimation circuit 21c estimates a power signal for each scan line in a power image and a velocity signal for each scan line in a velocity image based on the sampled harmonic component according to a procedure explained later.

The coordinate conversion memory for B-mode processing 23 and the coordinate conversion memory for color Doppler processing 25, respectively, convert signal arrays for each scan line input from the B-mode processing unit 19 or the color Doppler processing unit 21 into data for rectangular coordinates based on spatial information.

The image processing circuit 27 determines a signal value as a pixel value to be displayed in an image among a B-mode signal value B, a power signal value P and a velocity signal value V input from the coordinate conversion memories 23 and 25 for each pixel and assigns of one of the possible predetermined color and brightness according to the determined signal value. The detailed structure of the image processing circuit 27 will be described later.

The control circuit 31 is a central control unit for the whole system to control processes of the ultrasonic diagnostic apparatus 10 and may comprise a microcprocessor. The monitor 33, such as a CRT, etc., displays a tomographic image of the internal tissues of the object according to the input video signal. The monitor 33 may also display a compound image including B-mode, power and velocity signals produced by the image processing circuit 27. The console 35, connected to the apparatus 10, includes input devices (mouse, trackball, mode-change switches, keyboard, etc.) for an operator to input variety of directions, orders, information into a main unit 22 and to set an ROI, as well as other functions.

Image Processing Circuit

Figure 2:
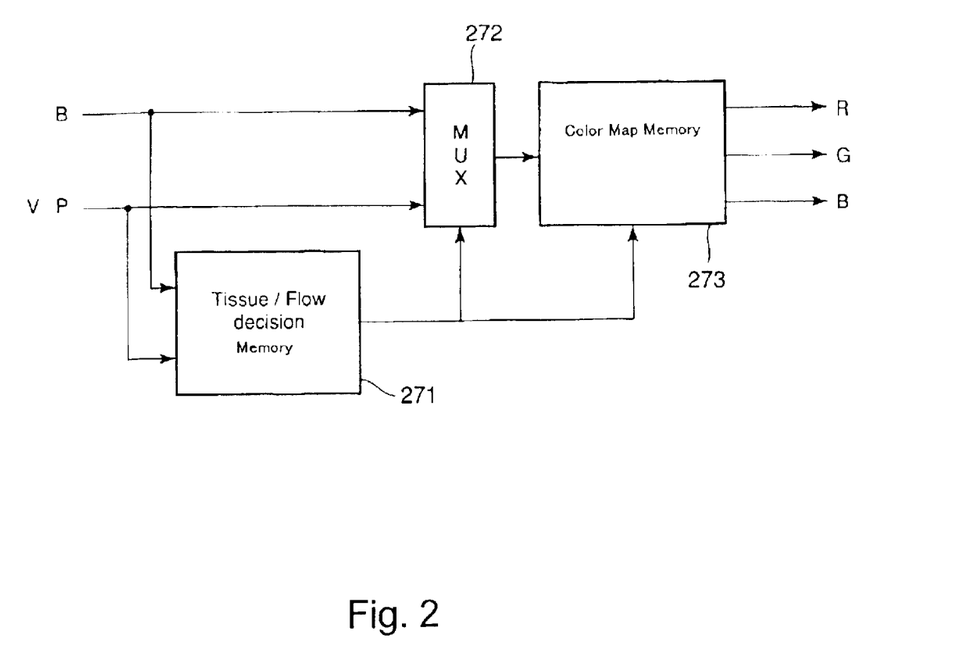
FIG. 2 is a block diagram of an image synthesizing circuit of a first embodiment of the invention.

The structure of the image processing circuit 27 will be explained next, referring to the block diagram in FIG. 2. The image processing circuit 27 includes a TFD (Tissue/Flow Decision) memory 271, a multiplexer 272, and a color map memory 273. The TFD memory 271 inputs a B-mode signal value and power signal value P for each pixel and decides which value (B or P) is to be used as a pixel value in an image according to a predetermined function table. The decided value for each pixel is output as signal value information to be used in the image from the TFD memory 271 to the multiplexer 272. The multiplexer 272 is a switch for selectively outputting one of the B, P, and V signal values for each pixel to the next device according to the decided signal value information. The color map memory 273 stores a color map to which the signal values are assigned. The color map memory 273 produces a compound image consisting of the B-mode, power and velocity signals by assigning a certain color and brightness to each pixel according to the signal value input from the multiplexer 272 and outputs the image to the monitor 33.

Acquiring/Processing/Displaying an Ultrasonic Image

Procedures of acquiring, processing, and displaying an ultrasonic image according to the ultrasonic diagnostic apparatus of the embodiment will be discussed, referring to FIGS. 3–9. These procedures make it possible to display an ultrasonic blood flow image indicating proper blood flow directions using a contrast medium and to clearly distinguish blood flow, contrast-enhancement in parenchyma and non-contrasted tissues on the image.

Acquiring an Ultrasonic Image

In this embodiment, a certain type of contrast medium (ex. "SonoVue™", produced by Bracco Research S.A.) may be used to create a second harmonic signal with a relatively large signal intensity (e.g., large enough to conduct a medical examination of an object) in a reflected echo when an ultrasonic wave with low (Mechanical Index is smaller than 0.1) acoustic pressure is transmitted. Such a condition may not meet the standard condition for the contrast medium recommended by the manufacturer, as most of the microbubbles in the medium are not collapsed. Therefore, fewer pseudo-Doppler signals, which do not indicate proper blood flow directions, are produced compared to the other contrast media suitable for higher MI. In addition, very little THI components due to the non-linearity of ultrasonic propagation are produced because of the low acoustic pressure (MI<0.1). If the intensity of the THI component is smaller than the level of the system noise, the components cannot be observed in an image. As a result, using harmonic components of the echo signal, a Doppler signal from the bubbles properly indicating a moving direction of the blood flow containing a contrast medium may be collected and thus a proper blood flow image may be obtained.

In this embodiment, a Phase Inversion Doppler method is used to image the harmonic components. In the Phase Inversion Doppler method, more than three pulses are used with different phases per scan line. This method is more advantageous in improving the axial resolution than the normal Doppler method (i.e., echo signals are acquired with the Doppler method using in-phase pulses and the harmonic components are imaged by filtering along the axial direction). However, this invention is not limited to Phase Inversion Doppler and the ultrasonic diagnostic apparatus 10 of the illustrated embodiment of the invention can obtain a satisfactory result with the above-mentioned Doppler method using the filtering procedure.

Figure 3:
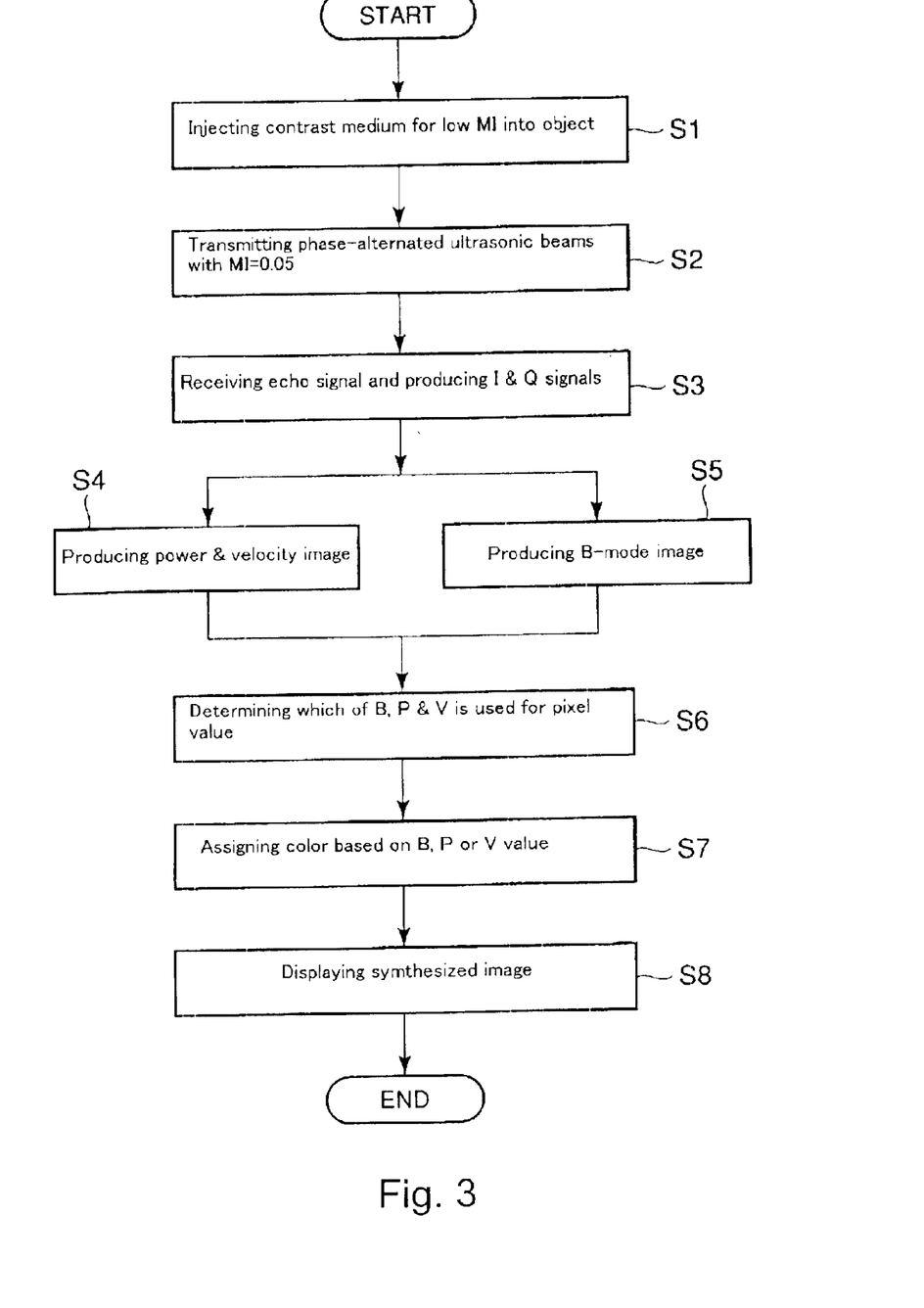
FIG. 3 is a flow chart showing processes of acquiring, processing, and displaying of an ultrasonic image according to the first embodiment.
Figure 4:
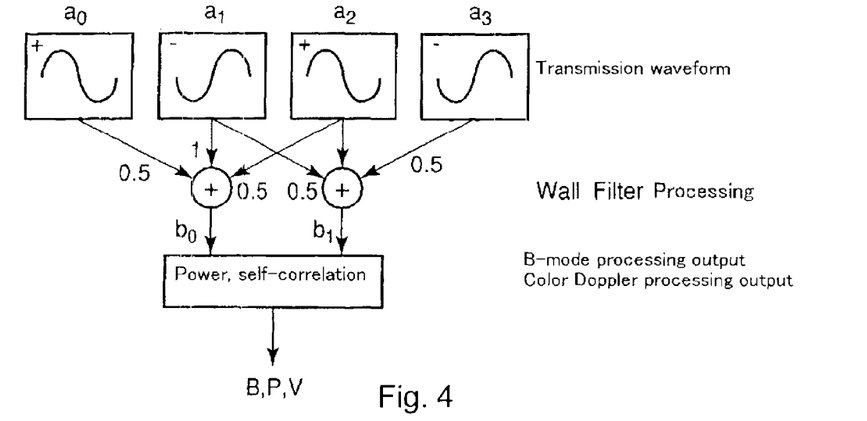
FIG. 4 is an illustration for an example of Phase Inversion Doppler method.

FIG. 3 shows a flow chart showing a series of processes of acquiring, processing and displaying of an ultrasonic image according to the first embodiment and FIG. 4 is an example illustration for explaining Phase Inversion Doppler method.

Referring to FIG. 3, the ultrasonic contrast medium is injected into the object (Step S1). As discussed above, with this contrast medium a second harmonic component with relatively a strong intensity can be received when an ultrasonic wave with low acoustic pressure (low MI) is transmitted. Next, according to a predetermined pulse sequence, a plurality of ultrasonic waves are transmitted to the object one after another, and the phase of the ultrasonic wave is reversed at every transmission (Step S2). As shown in the upper part of FIG. 4, the transmitter circuit 15 outputs transmission pulses to the probe 13 at a predetermined interval for each scan line (Pulse Repetition Frequency) with 180° phase reversal for each transmission. The probe 13 transmits ultrasonic waves according to the transmission pulses to the object. With a setting like MI=0.05, for example, almost no THI component is produced and collapse of the bubbles in the contrast medium may be suppressed. Therefore, very few pseudo-Doppler signals are produced. The transmission is performed at a lower portion of the frequency band of the probe such that the second harmonic components (twice the frequency of the transmitted ultrasonic wave) occur at the center of the probe characteristic.

Then, echo signals reflected from the object are received by the probe 13 to form RF signals in the receiver circuit 17 by a beam forming process, and the RF signals are transformed into I and Q signals at the baseband (Step S3). The I and Q signals are output to the B-mode processing unit 19 and the color Doppler processing unit 21. In the color Doppler processing unit 21, the I and Q signals are temporally stored and signals along the same scan line are output together to the wall filter 21b. The wall filter suppresses the fundamental components and samples the harmonic components by low-pass filtering as shown in the middle portion of FIG. 4. Based on the sampled harmonic components, a power signal for each scan line in a power image and a velocity signal for each scan line in a velocity image are estimated in the velocity/dispersion/power estimation circuit 21c as described below (Step S4).

If coefficients of the low pass filter are (0.5, 1.0, 0.5), representing respective coefficients in each of the following equations of b0 and b1, and signal values of four ultrasonic signals resulting from transmission pulses alternated by 180° from pulse to pulse for one scan line at a certain depth are $a_0$, $a_1$, $a_2$ and $a_3$, a power signal value P and a velocity signal value V at the depth can be obtained by the following equations:

$$P=\{|b_0|^2+|b_1|^2\}/2 \tag{1}$$

$$V=\tan^{-1}c \tag{2}$$

where $b_0 = 0.5\ a_0 + a_1 + 0.5\ a_2$ $b_1 = 0.5\ a_1 + a_2 + 0.5\ a_3$ $c = b_0^* \cdot b_1$ ($b_0^*$: complex conjugate of $b_0$)

Further, B-mode signals for each scan line in a B-mode image for imaging the fundamental components are obtained in the B-mode processing unit 19. Although only one received signal is enough to obtain a B-mode signal, signal to noise (S/N) ratio of the signal may be improved by the following procedure (Step S5).

If, similar to the above, values of four phase-inverted ultrasonic signals transmitted for one scan line and reflected at a certain depth are $a_0$, $a_1$, $a_2$, and $a_3$, a B-mode value B at the depth can be obtained by the following equation:

$$B=\{|a_0|^2+|a_1|^2+|a_2|^2+|a_3|^2\}/4 \tag{3}$$

Preferably the obtained B-mode, power and velocity signals are logarithmically compressed to be sent to the following unit. Although a velocity signal is not generally logarithmic compressed, it may be advantageous when the aliasing velocity is high or bubbles moving at a low speed and stationary tissues need to be distinguished. The signals B and P, obtained by equations (1) and (3), are logarithmic compressed and transformed to have an 8-bit length. For the signal V, a logarithmic compression may be performed by the following calculation:

$V_1 = (127/6)\log_2(|V_0|)(V_1 \geq 0)$ $V_1 = 0\ (V_1 < 0)$ $$V = \text{sign}(V_0) \cdot V_1, \tag{4}$$

where V=sign $(V_0) \cdot V_1$ is a function to output 1 or −1 according to the sign of $V_0$.

In an actual numerical example, when the transmission frequency is 1.5 MHz, the central reception frequency is 3 MHz and the RPF is 5 kHz, the aliasing velocity at the central frequency of the fundamental component (1.5 MHz)

is 128 cm/s and is 64 cm/s at the central frequency of the harmonic component (3 MHz). Under such conditions, aliasing would rarely occur when measuring blood flows in the abdomen. In addition, if the aliasing velocity is 64 cm/s, V is 127, V=64 corresponds to 8 cm/s and V=0 if smaller than 1 cm/s.

Figure 5:
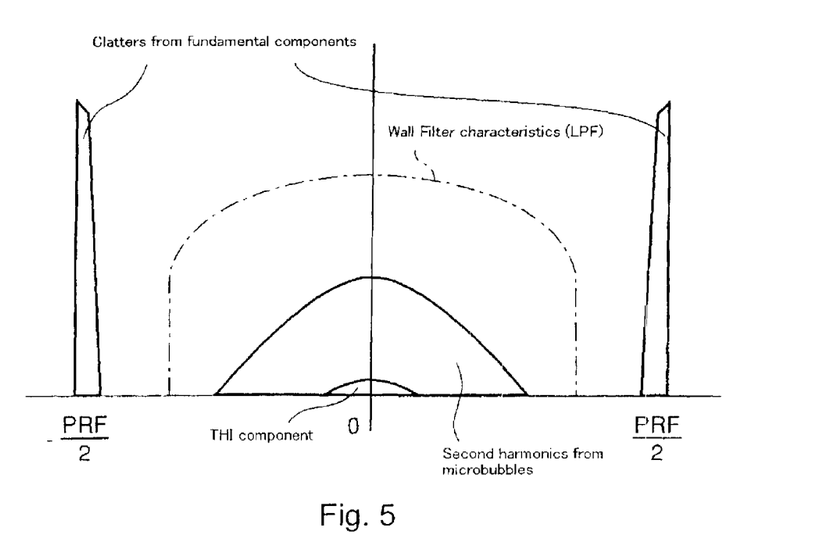
FIG. 5 shows an example of spectrum distribution of Doppler signals.

The low pass filter (LPF) characteristics of the wall filter are typically set to be (0.5, 1.0, 0.5) to suppress clatter components of the fundamental components as much as possible. The clatter signal of the fundamental component appears at the vicinity of ±PFR/2 as shown in FIG. 5. Although the clatter velocity in the abdomen measurements is usually smaller than 0.4 cm/s, the amplitude is large. Therefore, when an ultrasonic scan is performed with a broad reception frequency band or a small number of data arrays (four in this embodiment), the velocity distribution of the clatter may become broader under a spectrum broadening effect which broadens the Doppler spectrum. The remaining clatter of the fundamental component may badly affect the resulting image when it is erroneously recognized to be a signal of a high aliasing velocity in the second harmonic signal because the phase of the Doppler shift of the fundamental component is shifted by π, as compared to the non-Phase Inversion method. The Phase Inversion method using two sets of data is apt to be affected by the clatter. However, in this embodiment, the bad effect can be substantially reduced by the filter of (0.5, 1.0, 0.5) with three sets of data. Using an additional filter to suppress the fundamental component along the axial direction in the receiver circuit 17 would be more effective to remove the effect of the clatter of the fundamental component.

Further, the amount of the THI components in the detected second harmonic signals can be negligible because of the ultrasonic transmission with a small acoustic pressure. This may eliminate bad effects which often occur in conventional Doppler imaging without phase inversion, such as a motion artifact or a lower shift of the average velocity due to clatter. Accordingly, substantially low velocity can be observed in this embodiment.

Image Synthesizing Processing

Figure 6:
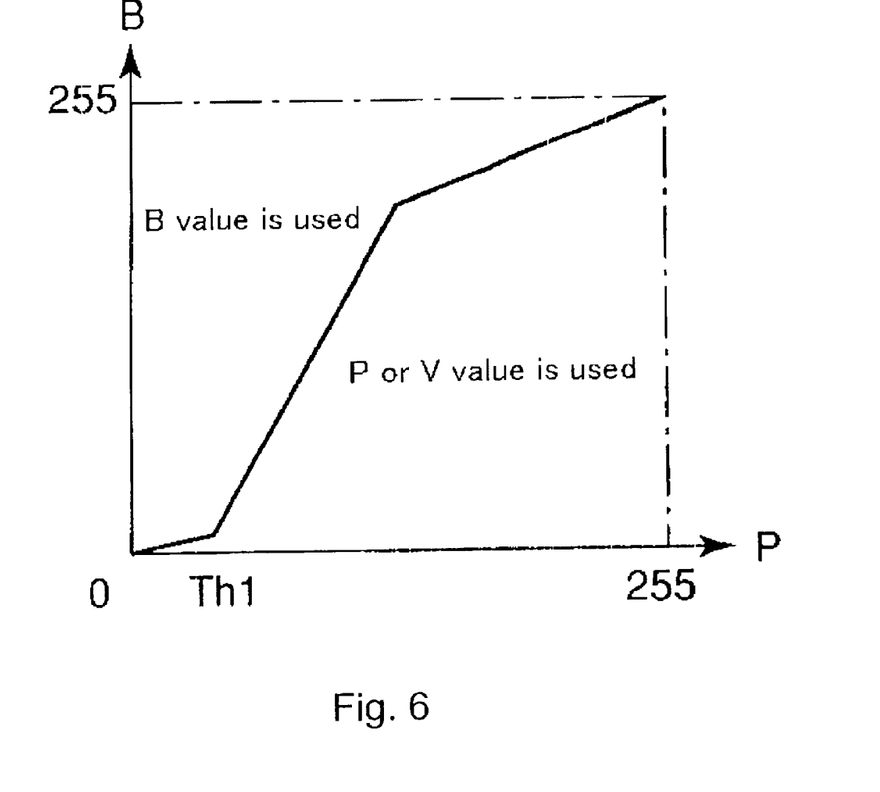
FIG. 6 shows an example of a function table for image processing of the first embodiment.
Figure 7:
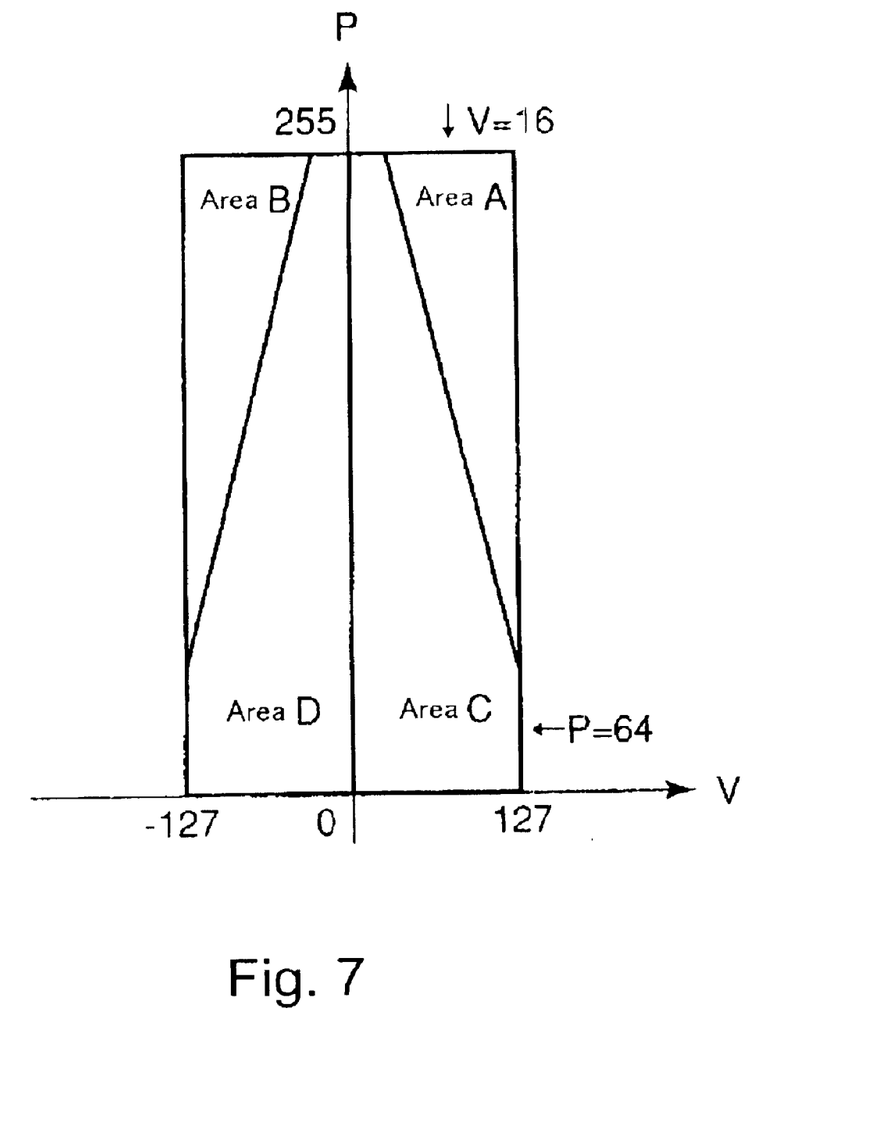
FIG. 7 shows a schematic example of a color map for image processing of the first embodiment.

Image synthesizing processes will be discussed next. In Step S6 in FIG. 3, which of the signals, B, P, or V, is used for a pixel value is determined according to the values of the signals B and P for the pixel. This determination may be qualitatively performed according to a function on table as shown in FIG. 6, for example. In this example, when the signal P of a pixel is substantially small (P<first threshold Th1), the value of the signal B is used as the pixel value. This is because the signal P is noise in many cases when P<Th1. On the other hand, when P>TH1 or P=Th1, the value of P or V is used because the value P represents blood flow information.

The threshold for the function table may not necessarily be a fixed value as long as the values B and P are to be compared to select one of them. For example, the function table in FIG. 6 determined by three linear functions. Thus the signal value information for each pixel is determined and sent to the multiplexer 272. The multiplexer 272 selectively outputs the signal value B, P, or V for each pixel according to the input information to the color map memory 273.

Then a color is assigned to each pixel in the color map memory 273 (Step S7), as in the following example. If the B value is used for the pixel, the color assignment is performed as Red=Green=Blue=B value (0–255), which means the pixel is displayed in gray scale. On the other hand, if the values P and V are used for the pixel, its color is assigned according to a color map divided into four areas based on the values of P and V. The following is an example of the coloring rule assuming P=0–255, V=(−128)–(+127):

Area A
Red is assigned. (when P>320−2·|V| and V≧0)
Red=min(1.12·P, 255)
Green=Blue=0.98·P
Area B
Blue is assigned. (when P>320−2·|V| and V<0)
Blue=min(1.12·P, 255)
Red=Blue=0.98·P
Area C
Red-Green is assigned. (when P<320−2·|V| and V≧0)
R1=min(1.12·P, 255)
G1=B1=0.98·P
R2=B2=0.9·P
G2=min(P·1.25, 255)
a=|V|/(160−P/2)
Red=a·R1+(1−a)·R2
Green=a·G1+(1−a)·G2
Blue=a·B1+(1−a)·B2
Area D
Blue-Green is assigned. (when P<320−2·|V| and V<0)
B1=min(1.12·P, 255)
R1=G1=0.98·P
R2=B2=0.9·P
G2=min(P·1.25, 255)
a=|V|/(160−P/2)
Red=a·R1+(1−a)·R2
Green=a·G1+(1−a)·G2
Blue=a·B1+(1−a)·B2

Figure 8:
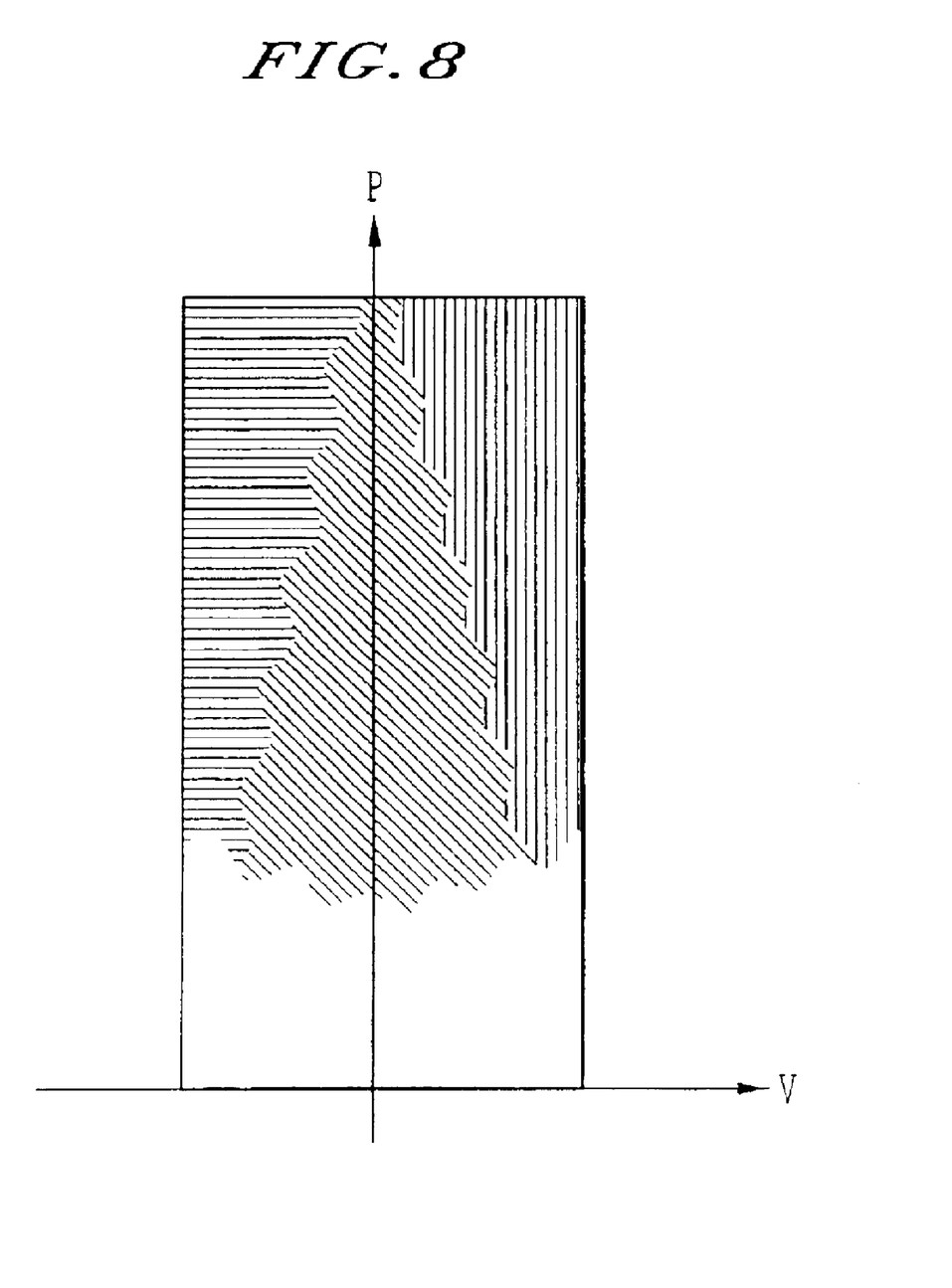
FIG. 8 shows an example of a color map for image processing of the first embodiment.
Figure 9:
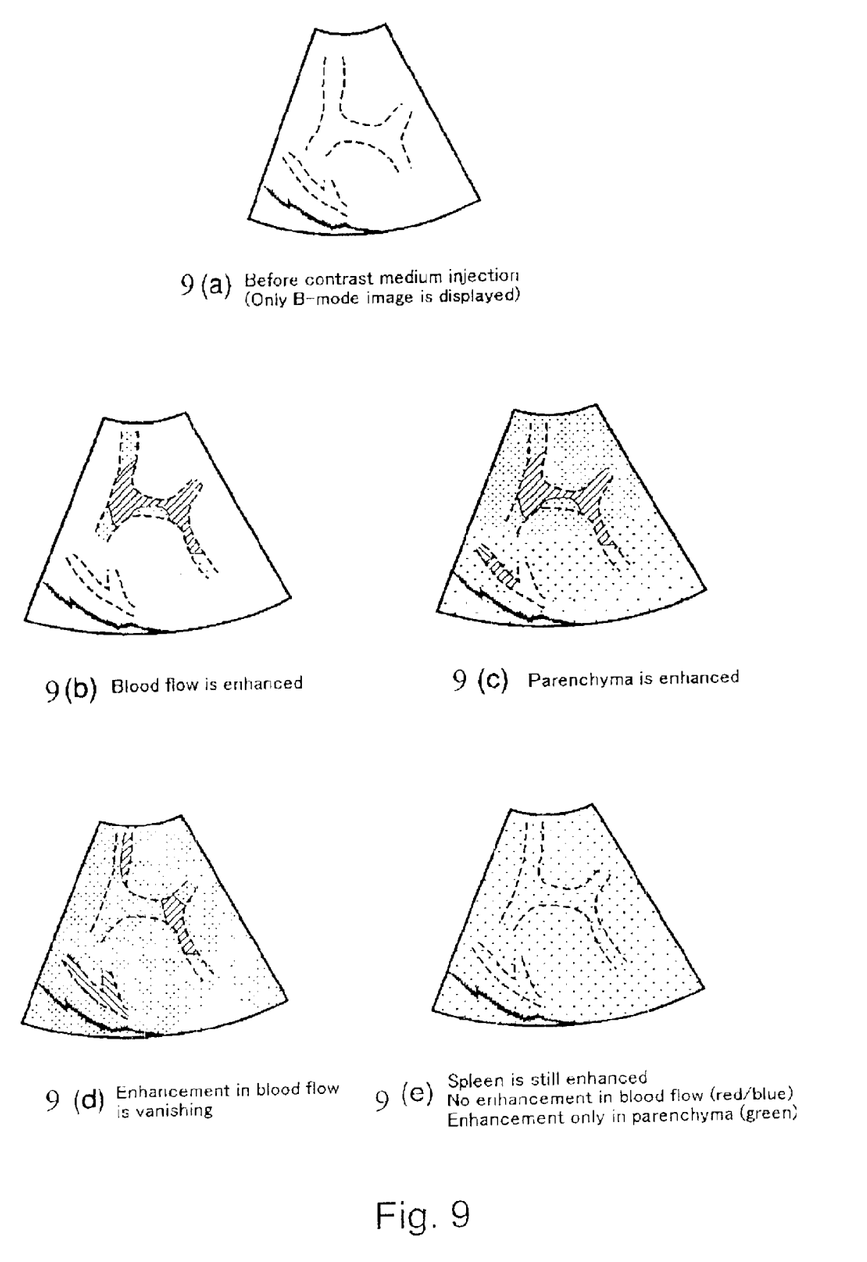
FIGS. 9A–9E are illustrations of images produced by an ultrasonic diagnostic apparatus according to the first embodiment of the invention.

Based on these processes, information of the object is displayed according to the color and brightness assignment as shown in a color map in FIG. 8.

(1) Bubbles flowing in a fast blood flow such in an artery: red or blue according to the direction;
(2) Bubbles in a slow blood flow in a vein: green;
(3) Bubbles in tissues: dark green because of the small velocity and power; and
(4) Non-contrast tissues: gray scale.

These four colors (red, blue, green and gray) gradually change at the boundaries and the color map can be manually determined by the operator observing the timing of contrast enhancement or continuity of blood cells displayed on the monitor 33. A remaining clatter in the fundamental component would have a fast velocity close to the Nyquist velocity as shown in FIG. 5 and its power is small due to the suppression by the LPF. When the velocity is close to the Nyquist and the power is small, the pixel is displayed with a color close to the grayscale. This makes it possible for the operator to observe an image as a B-mode tissue image while it actually is a power image.

Image Display Processing

Next the image synthesized with signals B, P, and V in the image processing circuit 27 is displayed in the monitor 33 (Step S8). Thus, the operator may observe the synthesized image.

The series of the procedures of steps S1–S8 discussed above are normally repeated in real time during an examination. This makes it possible for the operator to perform real time ultrasonic imaging at the monitor 33.

FIGS. 9(a)–(e) illustrate an example of synthesized images of a liver to be observed by the operator at the monitor. First, as shown in FIG. 9(a), since the signal intensity P is very small and there is no contrast enhancement before the contrast medium is injected, the value B is used for every pixel value to display a B-mode-only image. Then 5–10 seconds after the injection, the image shows large blood vessels enhanced with red or blue coloring as shown in FIG. 9(b). In this figure, hatched areas represent contrast-enhanced blood flows. According to the above-mentioned color assignment throughout FIGS. 9(a) to 9(e), right-slanted hatching corresponds to red and left-slanted hatching corresponds to blue. FIG. 9(c) shows the ultrasonic image 10–30 seconds after the injection in which the medium enters into the capillary vessels and the whole tissues (parenchyma) are enhanced. The dotted areas represent the enhanced parenchyma. These areas are colored in green. The areas where the medium does not enter (such as a diaphragm) are displayed as a B-mode image. Approximately 30–300 seconds after the injection, the contrast enhancement in the blood flow gradually diminishes in the displayed image as shown in FIG. 9(d). More than 5 minutes after the injection, as shown in FIG. 9(e), the displayed image shows enhanced parenchyma, such as a spleen or liver, in which the contrast medium tends to remain.

As discussed above, the ultrasonic diagnostic apparatus according to this embodiment is capable of imaging changes in time of bubbles as a synthesized image of B-mode, power and velocity signals with the Contrast Echo method.

The above-mentioned embodiment has some additional advantages. The ultrasonic diagnostic apparatus 10 of this embodiment does not suppress second harmonic signals from static tissues. This makes it possible to accurately calculate even a low velocity without a velocity-dependent effect of the wall filter.

The ultrasonic diagnostic apparatus 10 of this embodiment produces an ultrasonic image which indicates correct blood flow directions according to the power and blood velocity signals in a portion where blood flow information is available. In the parenchyma (tissue), it is possible to display an ultrasonic image in which blood flow, contrast-enhanced parenchyma and non-contrast tissues can be clearly distinguished since different colors are assigned according to the signal intensity.

Second Embodiment

In the first embodiment, a common transmission pulse is used for B-mode and color Doppler systems, while different transmission pulses are used in the second embodiment. For B-mode pulses at a transmission frequency suitable for imaging a fundamental component and for color Doppler, a transmission frequency suitable for harmonic imaging is used in this embodiment. This further improves the quality of an image obtained by an embodiment of this invention.

Third embodiment

In the first embodiment, B-mode images for observing tissues and power images and velocity images for blood flow are synthesized to be displayed. However, B-mode is not always needed for imaging tissues since the harmonic component may make the tissues visible due to the THI component, which may exist in a very small amount, or the fundamental component may make it visible due to slight asymmetry in the polarity of transmission pulses.

Since the amplitudes of these signals are small, they may be displayed in low brightness in the image. However, this is often an advantage in observing contrast-enhancement of parenchyma. In this embodiment, a switch for manually operating to turn on/off the B-mode image is additionally provided to the above-mentioned first or second embodiment.

Fourth Embodiment

In the first, second, and third embodiments, a B-mode image is produced by using the fundamental component, while in the fourth embodiment it is produced by the second harmonic component.

In Equations (1)–(3), information used in color Doppler (such as a P signal) is used as a B-mode signal. In this case, when a B-mode image is used for enhancement in parenchyma in image synthesizing, the resolution and sensitivity of the image will be increased. This is because B-mode image is higher in resolution and wider in the dynamic range than those of a color Doppler image.

Additionally, a signal other than that for color Doppler may be used to add information of a different type in the image. For example, using a signal $|a_0+a_1+a_2+a_3|$ is equivalent to using a wall filter $(1, 1, 1, 1)$ as a LPF. Since this is lower in cut-off frequency than a LPF $(0.5, 1, 0.5)$, it is more effective to suppress the high velocity or fundamental components and the resulting image is suitable for observing enhancement in parenchyma.

Fifth Embodiment

In the above-mentioned embodiments, 2D color Doppler scanning is used, while pulse Doppler is used in this embodiment. When a pulse Doppler scan is performed at a point on the same raster, the polarity of the pulse is reversed for each transmission, the LPF wall filter is used and the MI value is set lower than 0.1. This enables to display the result of Fast Fourier Transformation of a Doppler signal of contrast-enhancement of parenchyma or blood flow.

Sixth Embodiment

In this embodiment, the control circuit 35 controls the transmitter circuit 15 such that an ultrasonic wave with a high acoustic pressure (e.g. MI=0.8) to collapse the microbubbles in the contrast medium is transmitted. The control circuit 35 may be programmed to transmit the high acoustic pressure ultrasonic wave with a predetermined repetition time. Otherwise, the console 35 may provide thereon a switch (not shown) for the operator to manually transmit the high acoustic pressure wave anytime. The high acoustic pressure wave collapses the microbubbles and enhancement in a displayed image is cleared out, which enables the operator to observe replenishment of blood flow. Especially with the display mode as shown in this invention, the displayed image clearly shows blood flow flowing into tissues including parenchyma.

Numerous modifications and variations of the present invention are possible in light of the above technique. It is therefore to be understood that within the scope of the appended claims, the invention may be practiced otherwise than as specifically described herein.

Figure 10:
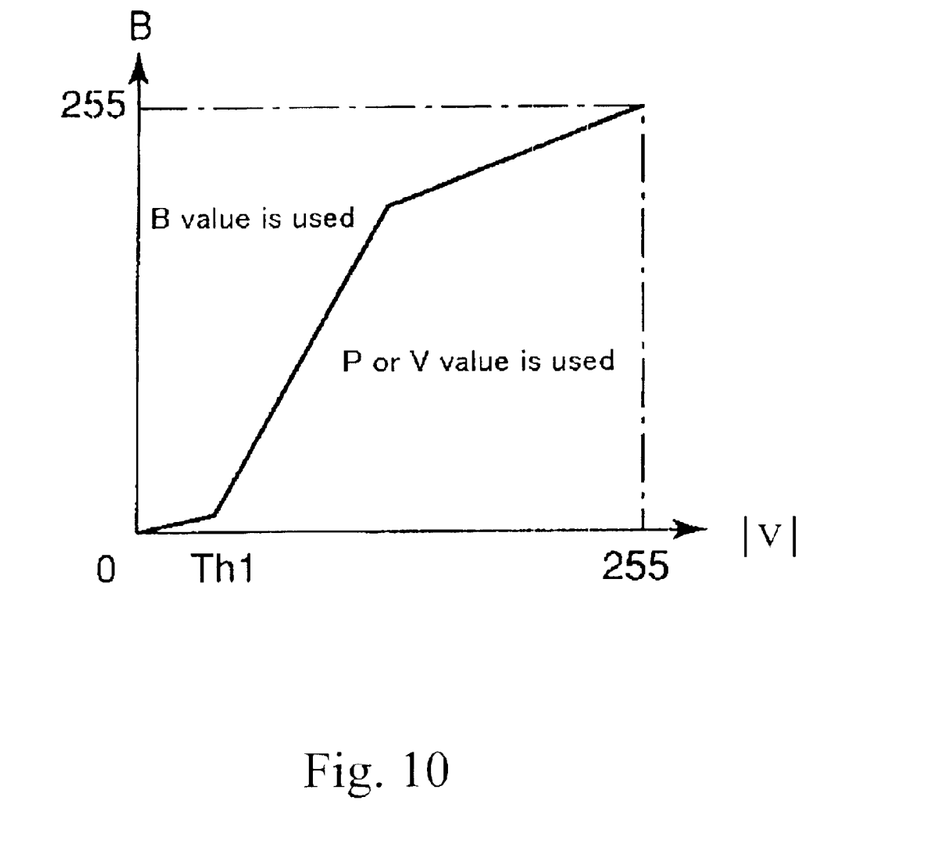
FIG. 10 represents an alternative function table for image processing.

For example, in Step S6 of FIG. 3, which of signal B or P is used as a pixel value is determined according to a function table defined by signals B and P as shown in FIG. 6. Instead, the determination may be made with a function table defined by signals B and V or signals B, P, and V. For example, if the absolute value of V is larger than a predetermined threshold, B is used for the pixel, as illustrated in FIG. 10. If the absolute value of V is not larger than a predetermined threshold, then the B–P table illustrated in FIG. 6 may be used.

As an alternative of the Phase Inversion Doppler method to obtain the harmonic component, a similar result may be obtained with a filter along the axial direction. Further, as a modification of the Phase Inversion Doppler method a transmission with a phase difference other than 180° (as taught in U.S. Pat. No. 6,155,981) and a wall filter (for obtaining a desired harmonic component resulting from the transmission) may be used.

Computer and System

The source of image data may be any appropriate image acquisition device such as an ultrasound machine and the like. Further, the acquired data may be digitized if not already in digital form. Alternatively, the source of image data being obtained and processed may be a memory storing data produced by an image acquisition device, and the memory may be local or remote, in which case a data communication network, such as PACS (Picture Archiving Computer System), can be used to access the image data for processing according to the present invention.

This invention conveniently may be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as ill be apparent to those skilled in the software art.

A computer implements the method of the present invention, wherein the computer housing houses a motherboard which contains a CPU, memory (e.g., DRAM, ROM, EPROM, EEPROM, SRAM, SDRAM, and Flash RAM), and other optical special purpose logic devices (e.g., ASICS) or configurable logic devices (e.g., GAL and reprogrammable FPGA). The computer may also include plural input devices, (e.g., keyboard and mouse), and a display card for controlling a monitor. Additionally, the computer may include a floppy disk drive; other removable media devices (e.g. compact disc, tape, and removable magneto optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

As stated above, the system includes at least one computer readable medium. Examples of computer readable media are compact discs, hard disks, floppy disks, tape, magneto optical disks, PROMS (e.g., EPROM, EEPROM, Flash EPROM), DRAM, SRAM, SDRAM, etc. Stored on any one or on a combination of computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g. computer code devices) which when executed by a computer causes the computer to perform the method of the present invention. The computer code devices of the present invention can be any interpreted or executable code mechanism, including but not limited to, scripts, interpreters, dynamic link libraries, Java classes, and complete executable programs. Moreover, parts of the processing of the present invention may be distributed for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuit, as will be readily apparent to those skilled in the art.

Additionally, the invention may be implemented on many varieties of ultrasound machines by installing software capable of harmonic TDI Doppler imaging and mapping using B, P, V, as evident to one of ordinary skill in the art.

Numerous modifications and variations of the present invention are possible in light of the above teachings. It is therefore to be understood that within the scope of the appended claim, the invention may be practiced otherwise than as specifically described herein.

What is claimed is:

1. An ultrasonic imaging apparatus for obtaining an ultrasonic image of an object having an ultrasonic contrast medium containing microbubbles injected in a blood flow, comprising:

a probe configured to transmit an ultrasonic beam and to receive an echo signal;

a probe driver configured to drive said probe to transmit the ultrasonic beam with a mechanical index value such that the microbubbles are collapsed to the extent that the echo signal contains at least one of velocity or direction information of the blood flow;

a separation unit configured to separate a harmonic signal from the echo signal;

a signal processing unit configured to obtain velocity and power values from the separated harmonic signal;

an image processing unit configured to produce an ultrasonic image from the echo signal wherein each pixel in the ultrasonic image has a color and brightness, wherein the color and brightness are determined according to the velocity and power values; and a display unit configured to display the ultrasonic image, wherein the color is at least one of a first color, a second color, and a third color, and wherein the imaging processing unit is further configured to assign the first color to a pixel if a corresponding echo signal represents a relatively fast motion and a first direction of the motion, the second color if the corresponding echo signal represents the relatively fast motion and a second direction of the motion, and the third color if the corresponding echo signal represents a relatively slow motion.

2. The ultrasonic imaging apparatus according to claim 1, wherein the signal processing unit is further configured to obtain a B-mode signal value from the echo signal.

3. The ultrasonic imaging apparatus according to claim 2, wherein the image processing unit further comprises:

a comparator configured to compare the B-mode signal value and at least one of the velocity and power value to determine whether the B-mode signal is to be used as the pixel value; and a color assigning unit configured to assign the color to the pixel, wherein the color is at least one of a first color and a second color that differs from the first color, based on at least one of the velocity and power values, the first color being assigned when the comparator determines that the B-mode signal value is used, and the second color being assigned when the comparator determines that the B-mode signal value is not used.

4. The ultrasonic imaging apparatus according to claim 3, wherein the color assigning unit is further configured to assign a brightness of the pixel according to at least one of the group consisting of the B-mode signal, velocity and power value.

5. The ultrasonic imaging apparatus according to claim 3, wherein the comparator is configured to determine based on a function table defined by a relationship between B-mode signal values and at least one of velocity or power values.

6. The ultrasonic imaging apparatus according to claim 1, wherein the mechanical index value is smaller than 0.1.

7. The ultrasonic imaging apparatus according to claim 1, further comprising:

a control unit configured to control the probe driver to transmit the ultrasonic beam with a mechanical index value such that the microbubbles are substantially collapsed at a predetermined timing.

8. The ultrasonic imaging apparatus according to claim 1, further comprising:
a switch configured to activate the probe driver to transmit the ultrasonic beam with a mechanical index value such that the microbubbles are substantially collapsed at a predetermined timing.

9. An ultrasonic imaging apparatus for obtaining an ultrasonic image of an object having an ultrasonic contrast medium containing microbubbles injected in a blood flow, comprising:
a probe configured to transmit an ultrasonic beam and to receive an echo signal;
a probe driver configured to drive said probe to transmit the ultrasonic beam with a mechanical index value such that the microbubbles are not substantially collapsed;
a separation unit configured to separate a harmonic signal from the echo signal;
a signal processing unit configured to obtain velocity, and power values from the separated harmonic signal;
an image processing unit configured to produce an ultrasonic image from the echo signal wherein each pixel in the ultrasonic image has a color and brightness, each of which is according to the velocity and power values; and
a display unit configured to display the ultrasonic images,
wherein the color is at least one of a first color, a second color, and a third color,
and wherein the imaging processing unit is further configured to assign the first color to a pixel if a corresponding echo signal represents a relatively fast motion and a first direction of the motion, the second color if the corresponding echo signal represents the relatively fast motion and a second direction of the motion, and the third color if the corresponding echo signal represents a relatively slow motion.

10. The ultrasonic imaging apparatus according to claim 9, further comprising:
a control unit configured to control the probe driver to transmit the ultrasonic beam with a mechanical index value such that the microbubbles are substantially collapsed at a predetermined timing.

11. The ultrasonic imaging apparatus according to claim 9, further comprising:
a switch configured to activate the probe driver to transmit the ultrasonic beam with a mechanical index value such that the microbubbles are substantially collapsed at a predetermined timing.

12. An ultrasonic imaging apparatus for obtaining an ultrasonic image of an object having an ultrasonic contrast medium containing microbubbles injected in a blood flow, comprising:
a transmitting/receiving unit configured to transmit an ultrasonic beam and to receive an echo signal at least from the microbubbles not collapsed by the ultrasonic beam;
a signal processing unit configured to obtain velocity and power values of the blood flow from the echo signal;
an image processing unit configured to produce an ultrasonic image from the echo signal, which includes a plurality of pixels colored according to the velocity and power values such that a first color is assigned to a first one of the pixels representing a velocity larger than zero, a second color is assigned to a second one of the pixels representing a velocity smaller than zero, and a third color is assigned to a third one of the pixels representing an absolute value of the velocity, which is smaller than a predetermined value; and
a display unit configured to display the ultrasonic image.

13. The ultrasonic imaging apparatus according to claim 12, further comprising:
a control unit configured to control the probe driver to transmit the ultrasonic beam with a mechanical index value such that the microbubbles are substantially collapsed at a predetermined timing.

14. The ultrasonic imaging apparatus according to claim 12, further comprising:
a switch configured to activate the probe driver to transmit the ultrasonic beam with a mechanical index value such that the microbubbles are substantially collapsed at a predetermined timing.

15. An ultrasonic imaging method for obtaining an ultrasonic image of an object having an ultrasonic contrast medium containing microbubbles injected in a blood flow, comprising:
transmitting an ultrasonic beam with a mechanical index value such that the microbubbles are collapsed to the extent that the echo signal contains at least one of velocity or direction information of the blood flow;
receiving an echo signal resulting from the ultrasonic beam;
separating a harmonic signal from the echo signal;
obtaining velocity and power values from the separated harmonic signal;
producing an ultrasonic image from the echo signal wherein each pixel in the ultrasonic image has a color and brightness,
wherein the color and the brightness are determined according to the velocity and power values; and
displaying the ultrasonic images
wherein the color is at least one of a first color, a second color, and a third color,
and wherein the imaging processing unit is further configured to assign the first color to a pixel if a corresponding echo signal represents a relatively fast motion and a first direction of the motion, the second color if the corresponding echo signal represents the relatively fast motion and a second direction of the motion, and the third color if the corresponding echo signal represents a relatively slow motion.

16. A computer program product stored on a computer readable medium storing instructions for execution on a computer system, which when executed by the computer system, causes the computer system to perform the method recited in claim 15.

17. An ultrasonic imaging method for obtaining an ultrasonic image of an object having an ultrasonic contrast medium containing microbubbles injected in a blood flow, comprising:
transmitting an ultrasonic beam with a mechanical index value such that the microbubbles are not substantially collapsed;
receiving an echo signal resulting from the ultrasonic beam;
separating a harmonic signal from the echo signal;
obtaining velocity and power values from the separated harmonic signal;

producing an ultrasonic image from the echo signal wherein each pixel in the ultrasonic image has a color and a brightness, wherein the color and the brightness are determined according to the velocity and power values; and displaying the ultrasonic images, wherein the color is at least one of a first color, a second color, and a third color, and wherein the imaging processing unit is further configured to assign the first color to a pixel if a corresponding echo signal represents a relatively fast motion and a first direction of the motion, the second color if the corresponding echo signal represents the relatively fast motion and a second direction of the motion, and the third color if the corresponding echo signal represents a relatively slow motion.

18. A computer program product stored on a computer readable medium storing instructions for execution on a computer system, which when executed by the computer system, causes the computer system to perform the method recited in claim 17.

19. An ultrasonic imaging method for obtaining an ultrasonic image of an object having an ultrasonic contrast medium containing microbubbles injected in a blood flow, comprising:

transmitting an ultrasonic beam;

receiving an echo signal at least from the microbubbles not collapsed by the ultrasonic beam;

obtaining velocity and power values of the blood flow from the echo signal;

producing an ultrasonic image from the echo signal, wherein the ultrasonic image includes a plurality of pixels being colored according to the velocity and power values wherein a first color is assigned to a first one of the pixels representing a velocity larger than zero, a second color is assigned to a second one of the pixels representing a velocity smaller than zero, and a third color is assigned to a third one of the pixels representing an absolute value of the velocity, which is smaller than a predetermined value; and displaying the ultrasonic image, wherein the color is at least one of a first color, a second color, and a third color, and wherein the imaging processing unit is further configured to assign the first color to a pixel if a corresponding echo signal represents a relatively fast motion and a first direction of the motion, the second color if the corresponding echo signal represents the relatively fast motion and a second direction of the motion, and the third color if the corresponding echo signal represents a relatively slow motion.

20. A computer program product stored on a computer readable medium storing instructions for execution on a computer system, which when executed by the computer system, causes the computer system to perform the method recited in claim 19.

* * * * *